United States Patent [19]

Choksi et al.

[11] Patent Number: 5,074,839
[45] Date of Patent: Dec. 24, 1991

[54] BLOOD TRANSFER APPARATUS

[75] Inventors: Pradip V. Choksi, Northridge; Thomas R. Thornbury, Granada Hills, both of Calif.

[73] Assignee: Hemotrans, Inc., Chatsworth, Calif.

[21] Appl. No.: 397,877

[22] Filed: Aug. 24, 1989

[51] Int. Cl.⁵ .............................................. A61M 37/00
[52] U.S. Cl. .................................. 604/4; 604/132; 604/408; 604/410
[58] Field of Search ................ 604/403, 408, 410, 4, 604/132, 133

[56] References Cited

U.S. PATENT DOCUMENTS

| | | |
|---|---|---|
| 2,597,715 | 5/1952 | Erikson . |
| 2,999,500 | 9/1961 | Schurer . |
| 3,032,037 | 5/1962 | Huber . |
| 3,089,493 | 5/1963 | Galindo . |
| 3,186,410 | 6/1965 | Buono . |
| 3,363,626 | 1/1968 | Bidwell et al. . |
| 3,381,687 | 5/1968 | Anderson et al. . |
| 3,680,560 | 8/1972 | Pannier et al. . |
| 4,033,345 | 7/1977 | Sorenson et al. . |
| 4,047,526 | 9/1977 | Reynolds et al. . |
| 4,048,994 | 9/1977 | Lo .................................... 604/142 |
| 4,397,643 | 8/1983 | Rygiel . |
| 4,573,992 | 3/1986 | Marx .................................. 604/408 |
| 4,642,088 | 2/1987 | Gunter ................................ 604/4 |
| 4,700,861 | 10/1987 | Neward .............................. 215/309 |
| 4,753,613 | 4/1988 | Bellin et al. ........................ 604/142 |
| 4,767,417 | 8/1988 | Boehringer . |
| 4,781,707 | 11/1988 | Boehringer et al. . |
| 4,850,964 | 7/1989 | Cotter ................................. 604/4 |

Primary Examiner—Stephen C. Pellegrino
Assistant Examiner—Michael Rafa
Attorney, Agent, or Firm—William W. Haefliger

[57] ABSTRACT

Blood and gas transfer apparatus comprises a substantially rigid receptacle; a collapsible bag in the receptacle, there being space formed between the bag and receptacle; structure in the receptacle forming first porting communicating with the bag and via which blood may be transferred into and out of the bag, and second porting communicating with that space between the bag and receptacle for selectively transferring gas into and out of the space; whereby in a first mode of operation blood may be drained into the bag via the first porting, and gas may be removed from the space via the second porting, and in a second mode of operation, blood may be drained from the bag via the first porting, and gas may be introduced into the space via the second porting, the structure including neck means on the receptacle and a cap received on the neck and forming the first and second porting.

8 Claims, 3 Drawing Sheets

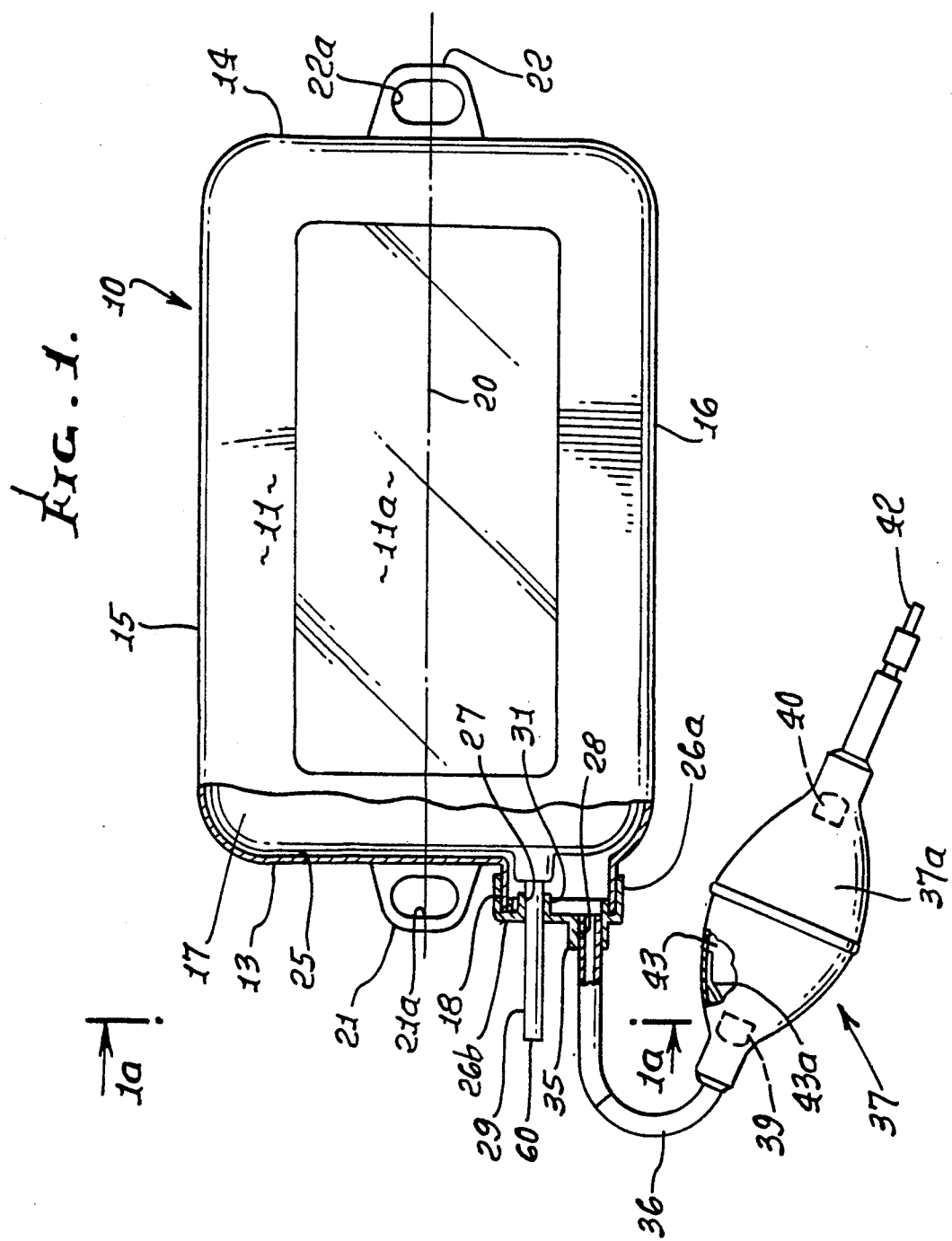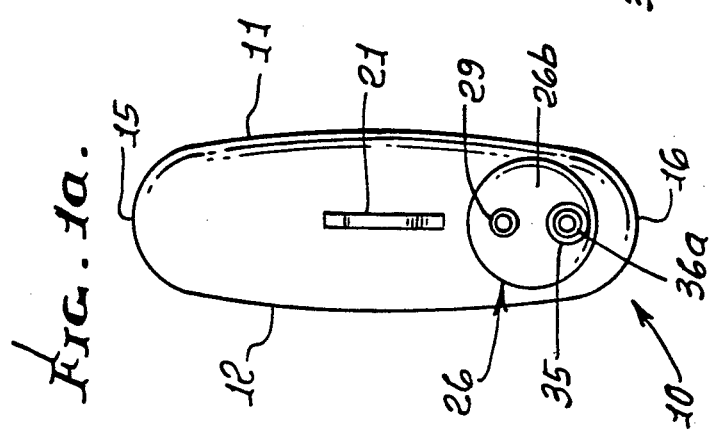

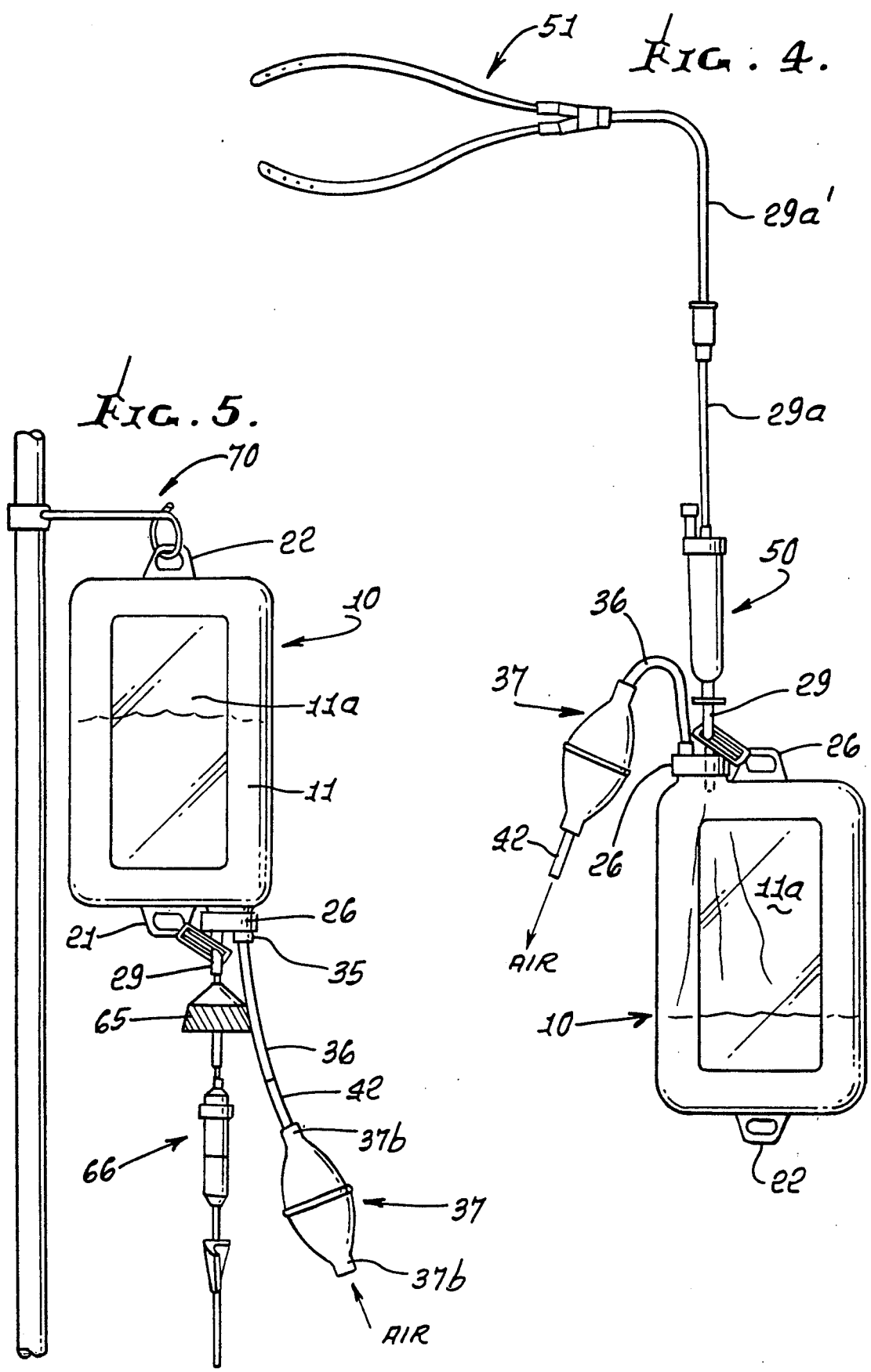

BLOOD TRANSFER APPARATUS

BACKGROUND OF THE INVENTION

This invention relates generally to autotransfusion apparatus, and more particularly to improvements in apparatus and procedures for accomplishing such transfusions.

Autologous blood transfusion has become very popular in recent months due to increased concern over transmission of diseases through banked blood. After a total joint replacement such as knee or hip, the wound continues to bleed for several hours. Normally this blood is collected in an evacuated container and discarded. But studies have shown that this blood is of high quality and can be reinfused.

Prior devices to accomplish such transfusions employ flexible bags in rigid outer containers, the container in one position adapted to receive blood from a patient to fill the bag; and in an inverted position of the container the blood drains from the enclosed bag. In a typical procedure, anticoagulant is added to the bag through an injection site in inlet tubing. Great care is taken to keep the bag upright to prevent the liquid anticoagulant from entering the evacuation tube that contains the hydrophobic filter. If this filter chamber gets filled with the liquid during the blood collection process then the unit cannot be evacuated and air in the container cannot be displaced by the incoming blood. The unit is thus rendered inoperative and has to be discarded or the filter has to be replaced.

After blood is collected in the bag, the unit is disconnected from the drain and prepared for re-infusion. To re-infuse the collected blood, any air in the bag is expelled by infusing air into the interstitial space surrounding the bag.

Disadvantages with such prior devices include:

1. The bag has to be kept upright during the entire collection procedure. This is not very easy because the bag has to be handled several times during patient transfer from the operating room to recovery room to floor. With the hydrophobic filter covered in liquid, the unit becomes inoperative and there is no indicator to tell the nurse that the unit has become inoperative.

2. The activation of vacuum requires availability of wall suction with accurate vacuum regulator. If the regulator is set too high, the outer bottle collapses and the unit becomes inoperative. High vacuum could also cause hemolysis of the blood.

3. The flow-through system of evacuation causes an air-blood interface. This can lead to hemolysis.

4. The air in the bag at the end of collection has to be expelled prior to re-infusion. This is an awkward maneuver and sometimes causes blood to squirt out of the bag.

5. The device has no means of indicating the presence of vacuum in the system.

6. The device has no graduations to indicate volume during re-infusion.

7. The device is quite complicated to use, and inadvertent clamping or unclamping of tubes or tipping the unit can lead to malfunctioning of the unit.

There is need for improved apparatus to accomplish such blood transfer.

SUMMARY OF THE INVENTION

It is a major object of the invention to provide improved apparatus and procedures overcoming the above disadvantages. Basically, the device of the invention comprises:

a) a substantially rigid receptacle, b) a collapsible bag in the receptacle, there being interstitial space formed between the bag and receptacle, c) structure in the receptacle forming first porting communicating with the bag and via which blood may be transferred into and out of the bag, and second porting communicating with the space between the bag and receptacle for selectively transferring gas into and out of the space, d) whereby when the receptacle is suspended in a first position blood may be drained into the bag via the first porting, and gas may be removed from the space via the second porting, and when the receptacle is suspended in a second position, blood may be drained from the bag via the first porting, and gas may be introduced into said space via the second porting.

As will be seen, the receptacle is typically elongated and has opposite ends, and the said structure is located at one of said ends. Also, the structure advantageously includes neck means on the receptacle and cap means received on the neck means and forming the first and second porting. A tube is typically connected with the collapsible bag to pass blood into and out of the bag, the tube received through said first porting, and the tube may extend through the container structure neck, and through first porting in the cap. A line is typically connected with the first porting for flowing blood from a patient to and through said first opening and into the bag.

It is another object of the invention to provide manually manipulable pump means operatively connected with said second porting, for selectively pumping gas into or out of the interstitial space.

These and other objects and advantages of the invention, as well as the details of an illustrative embodiment, will be more fully understood from the following specification and drawings, in which:

DRAWING DESCRIPTION

FIG. 1 is a side elevation showing apparatus incorporating the invention;

FIG. 1a is an end view taken on lines 1a-1a of FIG. 1;

FIG. 4 is a view like FIG. 3, showing transfer of blood from a patient into the bag in the apparatus; and FIG. 5 is an elevation showing the apparatus inverted, and suspended, for draining of blood from the bag.

DETAILED DESCRIPTION

Figure 3:
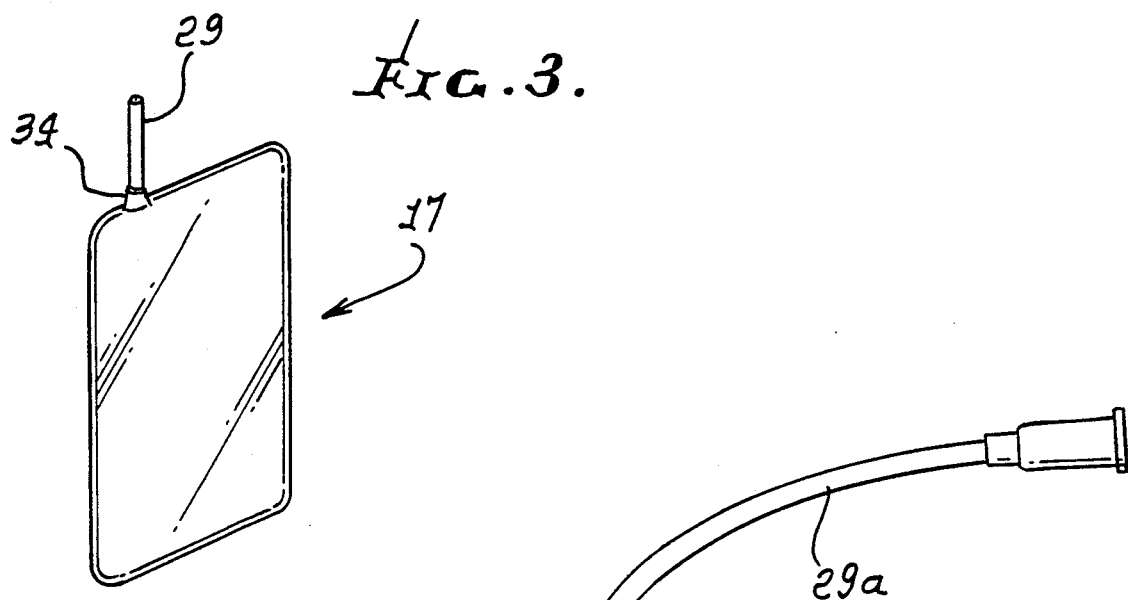
FIG. 3 is a perspective view of a bag employed in the FIG. 1 and 2 apparatus.
Figure 2:
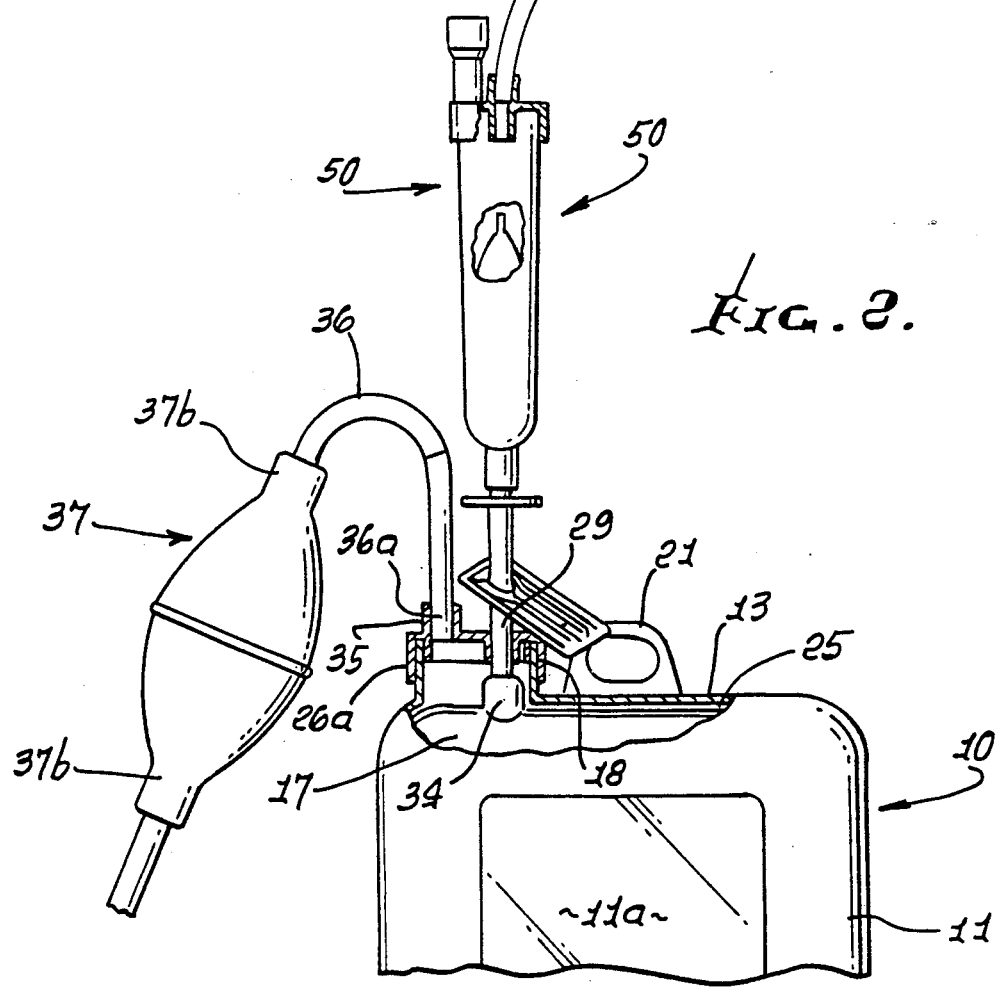
FIG. 2 is a fragmentary elevation showing filling of the bag in the FIG. 1 apparatus.

Referring to the drawings; a substantially rigid receptacle or container 10 has thin opposite side walls 11 and 12, end walls 13 and 14, and edge walls 15 and 16. Walls 11, 12, 15 and 16 are longitudinally elongated, and curved, as shown. The receptacle is typically molded from plastic material, and the walls are transparent to permit viewing of a blood receiving bag 17 in the receptacle. Interstitial space 25 is formed between the bag and the described walls. See wall transparent zone 11a.

A neck means or structure 18 is integral with end wall 13, near one end thereof, and a suspension flange 21 is located medially of wall 13, to be intersected by the longitudinal central axis 20 of the structure. A similar flange 22 is located medially of wall 14, to be intersected by axis 20. Flanges 21 and 22 are integral with the respective walls 13 and 14, for suspending the receptacle as seen in FIGS. 4 and 5. They contain suspension openings 21a and 22a.

Structure is located on the receptacle to form first porting communicating with the bag and via which blood may be transferred into and out of the bag, and second porting communicating with said space between the bag and receptacle for selectively transferring gas into and out of said space. Such structure advantageously includes a rigid closure cap 26 having a skirt 26a received on and attached to the neck 18, as shown, the cap also having an end wall 26b forming the described first porting at 27, and second porting at 28. A tube 29 attached to the bag 17 at 34 communicates with the bag interior, and the tube may be passed through the bore 27 of a cap second skirt 31 integral with wall 26b to seal-off against that bore. Straight bore 27 supports tube 29 to project as shown. The tube and bag may consist of elastomeric material, and the bag may be introduced into the interior space of the receptacle via the neck, i.e., before attachment of the cap skirt to that neck, to orient bore 27 and a shirt 35. Tube 29 is located to only fit bore 27. Bore 27 forms the first porting, as referred to.

A third cap skirt 35 carried by end wall 26b is adapted to telescopically receive the end 36a of tubing 36 extending from a manually manipulable (squeezable) pump unit 37. The latter contains appropriate valving indicated at 39 and 40 such that when the pump body 37a is squeezed, valve 40 opens and valve 39 closes, so that air is expelled at 42, and when the pump body resiliently expands, valve 39 opens and valve 40 closes, to withdraw air from space 25 into the interior 43 of the pump. Flat metallic spring means may be located in interior 43, to assist expansion of the body. See spring 43a, for example.

Skirt 35 forms a nipple to which the tubing 36 attaches. The nipple forms a bore that defines the second porting as referred to.

Accordingly, when the receptacle is suspended in a first position, as seen in FIG. 4, blood may be drained into the bag via the first porting 27 and tube 29, and gas such as air may be removed from the interstitial space 25 via the the second porting 28. See also filter unit 50, in series with blood collector 51 and tubes 29a, 29a' and 29. When the receptacle is suspended in inverted second position by means 70, as seen in FIG. 5, blood may be drained from the bag, via first porting, and tube 29, and gas such as air flows into the interstitial space 25, as via the second porting 28. To this end, the pump unit 37 may be endwise reversed, so that the pump may be repeatedly squeezed to force gas or air into the space 25 to pressurize the bag, collapsing it while blood is forced out via tubing 29 and apparatus 66. See pump body tubular ends 37b that interchangeably fit tube 36.

Unusual advantages include the following:

1. Closed systems. Single port for entry and exit of blood.

2. Simple system. Less likelihood of operator error.

3. Anticoagulant injection port directs the liquid into the bag, through the filter.

4. No blood-air interface. Hence reduced hemolysis.

5. Built-in vacuum bulb for applying suction.

6. Bulb set at the right level of vacuum for optimum drainage without hemolysis.

7. Bulb acts as an indicator of vacuum.

8. The system is compact. Tubings do not drag on the floor during collection procedure.

9. At the time of re-infusion, no need to expel air from the bag since the volume of air in the bag is insignificant.

10. Blood can be re-infused by gravity or under pressure using the built-in bulb.

11. Graduations to show volume of blood during both collection and re-infusion.

12. The unit can be placed on its side, or inverted, without malfunction.

To operate the unit, 40 ml of anticoagulant is injected into the injection port at tube end 60. It is not necessary to hold the collection bag in any particular orientation since no hydrophobic filter is employed. The bag is hooked up to the wound drain (blood collector) at 51 and collection starts under gravity flow, via tubing 29 and 29a.

To start the drain under vacuum, the nurse needs to squeeze the bulb 37a several times to evacuate the air in the interstitial space surrounding the bag. The resiliency of the bulb determines the level of vacuum applied. For example, set it at $-50$ to $-100$ mm of Hg. A collapsed bulb is an indication of presence of vacuum. Blood is collected in the bag as shown in FIG. 4.

When the bag is ready to be re-infused there is no need to expel air from the bag because there is no significant volume of air in the bag. The drain line is disconnected and discarded and a transfusion set with 40 micron filter 65 and a tubular drip chamber 66 is connected to the bag, via elongated tube 29 projecting externally through the cap 26. For gravity re-infusion, the pressure/vacuum bulb is disconnected and discarded. For pressure re-infusion, the bulb is reversed to pressurize the interstitial space as described.

Of additional advantage is the fact that the receptacle and bag may be flatly horizontally supported, as for example, on a bed and between a patient's legs, during blood flow into and out of the bag. This is enabled due to use of the pump means and lack of hydrophobic filter as referred to.

We claim:

1. In blood and gas transfer apparatus, the combination comprising a) a substantially rigid receptacle, b) a collapsible bag in the receptacle, there being space formed between the bag and receptacle, c) structure in the receptacle forming first porting communicating with the bag and via which blood may be transferred into and out of the bag, and second porting communicating with said space between the bag and receptacle for selectively transferred gas into and out of said space, d) whereby in a first mode of operation blood may be drained into the bag via said first porting, and gas may be removed from said space via said second porting, and in a second mode of operation, blood may be drained from the bag via said first porting, and gas may be introduced into said space via said second porting, e) said structure including neck means on the receptacle and cap means received on the neck means and forming said first and second porting, f) and including manually manipulable pump means operatively connected with said second porting, for selectively pumping gas into or out of said space, via tubing connected to the second porting, the pump means having a manually squeezable bulbous body and opposite ends interchangeably connectable with tubing extending to said second porting, g) the cap means having a rigid end wall, a rigid skirt integral with said end wall and projecting exteriorly of the cap means, said skirt forming said second porting, there being flexible tubing attached to the skirt and to one of said opposite ends of the pump means body.

2. The apparatus of claim 1 wherein said receptacle is elongated and has opposite ends, and said structure is located at one of said ends.

3. The apparatus of claim 2 including means on the receptacle and offset from the cap means for suspending the receptacle with the cap means presented upwardly, and alternatively for suspending the receptacle with the cap means presented downwardly.

4. The apparatus of claim 2 including a tube connected with the bag to pass blood into and out of the bag, the tube received through said first porting.

5. The apparatus of claim 3 including a tube connected with the bag to pass blood into and out of the bag, the tube extending in said neck means and through said first porting in said cap means.

6. The apparatus of claim 1 including a line operatively connected with said first porting for flowing blood from a patient to and through said first porting and into the bag.

7. The apparatus of claim 1 wherein the receptacle is endwise suspended, so that said structure is above or below the bag.

8. The apparatus of claim 1 wherein the bag and receptacle lie flatly horizontally and said pump means is operable to assist blood flow into and out of the bag.

* * * * *

UNITED STATES PATENT AND TRADEMARK OFFICE
CERTIFICATE OF CORRECTION

PATENT NO.   :   5,074,839
DATED        :   December 24, 1991
INVENTOR(S)  :   Pradip V. Choksi, Thomas R. Thornbury & Julie A. Ryan It is certified that error appears in the above-identified patent and that said Letters Patent is hereby corrected as shown below:

On the title page, 75 Inventors: should read:

--Pradip V. Choksi, Northridge;
  Thomas R. Thornbury, Granada Hills, both of Calif.,
  and Julie A. Ryan, Westlake, California--

Signed and Sealed this

Eleventh Day of April, 1995

Attest:

BRUCE LEHMAN

Attesting Officer        Commissioner of Patents and Trademarks